US012805926B2

(12) United States Patent
Lee et al.

(10) Patent No.: US 12,805,926 B2
(45) Date of Patent: Nov. 24, 2026

(54) CAPSULORHEXIS APPARATUS, SURGICAL APPARATUS, AND METHOD FOR APPLYING ELECTRIC PULSE TO SURGICAL APPARATUS

(71) Applicant: TI INC., Gyeonggi-do (KR)

(72) Inventors: Hong Jai Lee, Seoul (KR); Sung Hyuk Moon, Busan (KR); Jae Wook Yang, Busan (KR); Seung Jai Lee, Gyeonggi-do (KR); Sun Joon Hwang, Gyeonggi-do (KR); Hyun Jeong Kang, Gyeonggi-do (KR)

(73) Assignee: TI INC., Gyeonggi-do (KR)

( * ) Notice: Subject to any disclaimer, the term of this patent is extended or adjusted under 35 U.S.C. 154(b) by 753 days.

(21) Appl. No.: 17/604,382

(22) PCT Filed: Dec. 3, 2020

(86) PCT No.: PCT/KR2020/017546
§ 371 (c)(1),
(2) Date: Oct. 15, 2021

(87) PCT Pub. No.: WO2021/118161
PCT Pub. Date: Jun. 17, 2021

(65) Prior Publication Data

US 2022/0192730 A1 Jun. 23, 2022

(30) Foreign Application Priority Data

Dec. 11, 2019 (KR) ........................ 10-2019-0165068

(51) Int. Cl.
*A61B 18/14* (2006.01)
*A61B 18/00* (2006.01)
(Continued)

(52) U.S. Cl.
CPC ........ *A61B 18/148* (2013.01); *A61B 18/1206* (2013.01); *A61F 9/00754* (2013.01);
(Continued)

(58) Field of Classification Search
CPC ........ A61B 18/148; A61B 2018/00083; A61B 2018/00107; A61B 2018/00321; A61B 2018/00767; A61F 9/00754
See application file for complete search history.

(56) References Cited

U.S. PATENT DOCUMENTS 5,088,997 A 2/1992 Delahuerga et al.
5,697,090 A 12/1997 Iura
(Continued)

FOREIGN PATENT DOCUMENTS

JP 2013-528447 7/2013
KR 10-2011-0084887 7/2011
(Continued)

OTHER PUBLICATIONS

U.S. Appl. No. 62/872,494, filed Jul. 10, 2019, Doraiswamy, Anand.*
(Continued)

*Primary Examiner* — Annie L Shoulders
(74) *Attorney, Agent, or Firm* — WOMBLE BOND DICKINSON (US) LLP

(57) ABSTRACT

A surgical apparatus for making an incision in a living tissue according to the present disclosure includes a hand piece including a loop-type electrode part and a generator configured to transmit electrical energy to the electrode part, wherein the generator applies electric-field pulse waveforms made of two consecutive pulse groups to the electrode part, the two consecutive pulse groups include a first pulse group and a second pulse group, each pulse group includes mini-pulses, a peak voltage of the first pulse group is less than a
(Continued)

peak voltage of the second pulse group, and a duration of the first pulse group is longer than a duration of the second pulse group.

13 Claims, 12 Drawing Sheets

(51) Int. Cl.
*A61B 18/12* (2006.01)
*A61F 9/007* (2006.01)

(52) U.S. Cl.
CPC ............... *A61B 2018/00083* (2013.01); *A61B 2018/00107* (2013.01); *A61B 2018/00321* (2013.01); *A61B 2018/00601* (2013.01); *A61B 2018/00767* (2013.01); *A61B 2018/0091* (2013.01); *A61B 2018/1407* (2013.01)

(56) References Cited

U.S. PATENT DOCUMENTS

| | | | | |
|---|---|---|---|---|
| 5,766,153 | A | 6/1998 | Eggers et al. | |
| 6,352,535 | B1 | 3/2002 | Lewis et al. | |
| 6,364,877 | B1 | 4/2002 | Goble et al. | |
| 2006/0142750 | A1* | 6/2006 | Da Silva | A61B 18/082 606/27 |
| 2011/0118734 | A1* | 5/2011 | Auld | A61F 9/00754 606/45 |
| 2011/0213359 | A1 | 9/2011 | Ben-Nun et al. | |
| 2012/0078242 | A1* | 3/2012 | Jia | A61F 9/00754 606/32 |
| 2014/0207137 | A1* | 7/2014 | Keller | A61F 9/0079 606/107 |
| 2015/0216727 | A1 | 8/2015 | Keller | |
| 2017/0000646 | A1* | 1/2017 | Moon | A61F 9/00754 |
| 2021/0186605 | A1* | 6/2021 | Jackson | A61B 18/1492 |
| 2022/0142817 | A1* | 5/2022 | Doraiswamy | A61P 27/00 |

FOREIGN PATENT DOCUMENTS

| | | |
|---|---|---|
| KR | 10-2012-0046209 | 5/2012 |
| KR | 10-2014-0104584 | 8/2014 |
| KR | 10-1484418 | 1/2015 |
| WO | 2019/027081 | 2/2019 |

OTHER PUBLICATIONS

U.S. Appl. No. 62/874,946, filed Jul. 16, 2019, Doraiswamy, Anand.*
U.S. Appl. No. 62/945,160, filed Dec. 8, 2019, Doraiswamy, Anand.*
Office Action mailed on Apr. 27, 2022 for Korean Patent Application No. 10-2019-0165068 and its English translation from Global Dossier.
Extended European Search Report dated Nov. 22, 2023 for European Patent Application No. 20900392.0.
International Search Report for PCT/KR2020/017546 mailed on Jun. 8, 2021 and its English translation from WIPO (now published as WO 2021/118161).
Written Opinion of the International Searching Authority for PCT/KR2020/017546 mailed on Jun. 8, 2021 and its English translation by Google Translate (now published as WO 2021/118161).
Office Action dated Jun. 16, 2021 for Korean Patent Application No. 10-2019-0165068 and its English translation by Google Translate.

* cited by examiner

[FIG. 1]
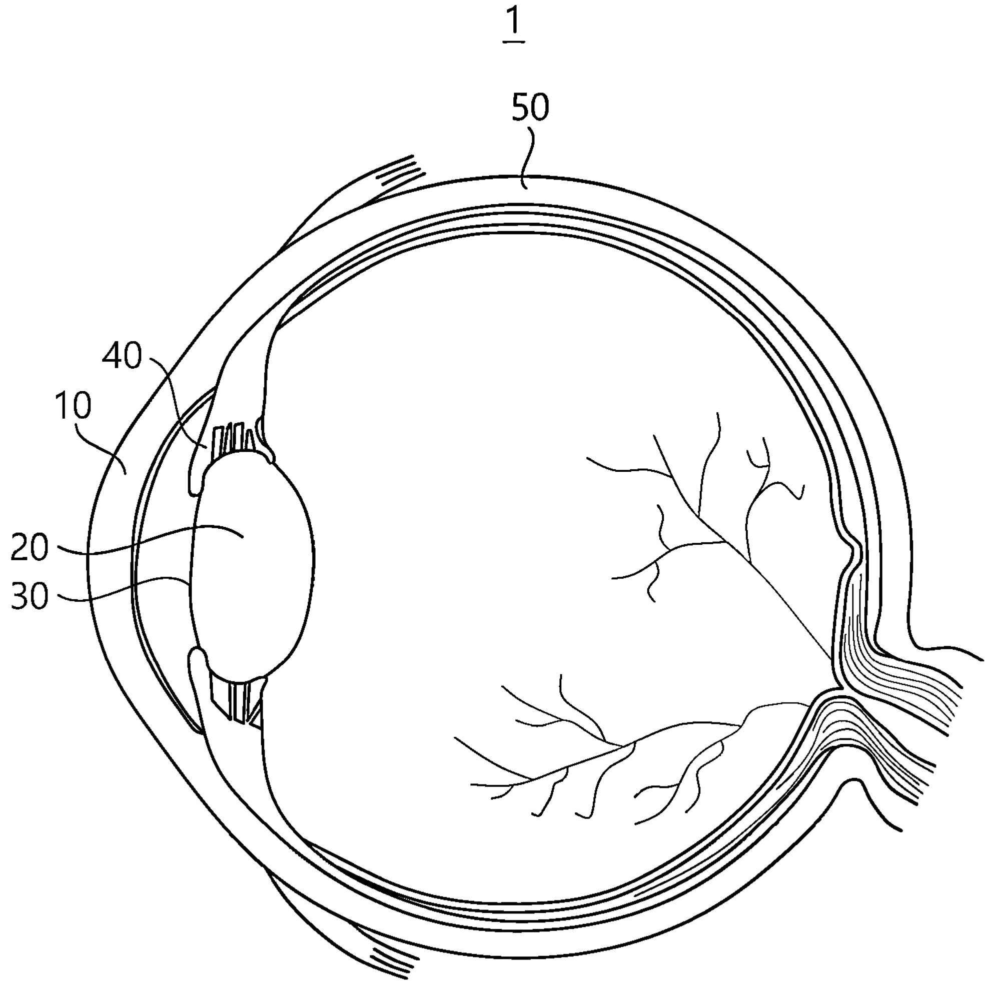

[FIG. 2]
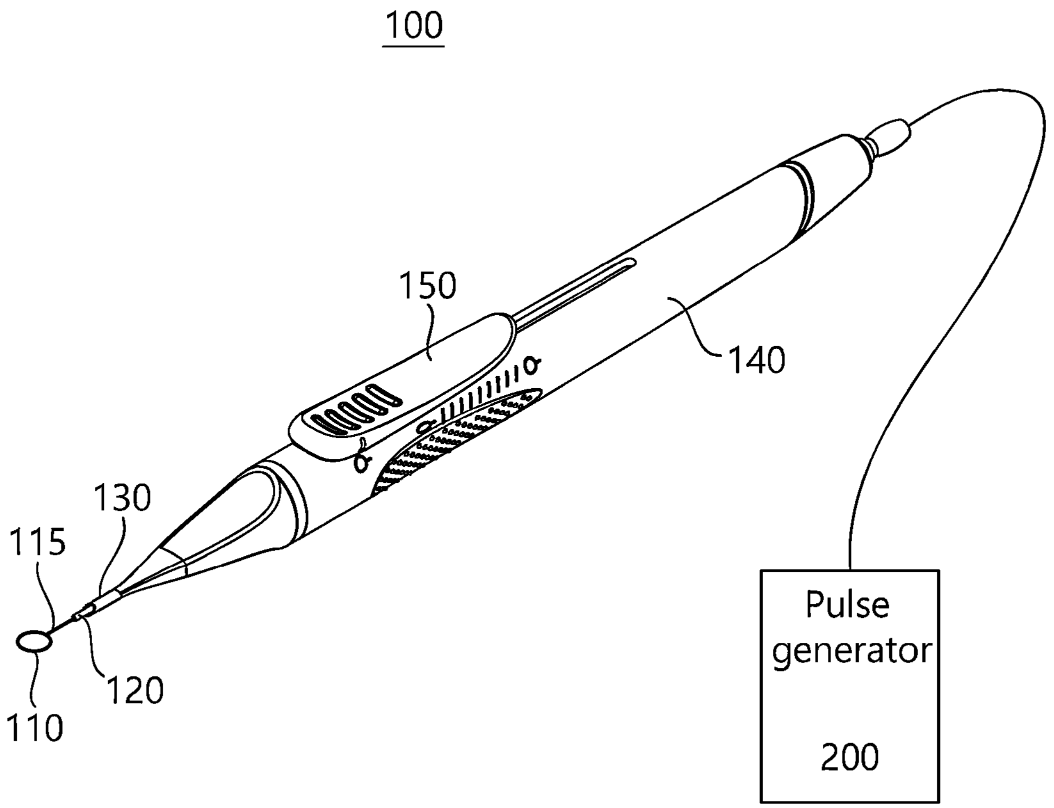

[FIG. 3]
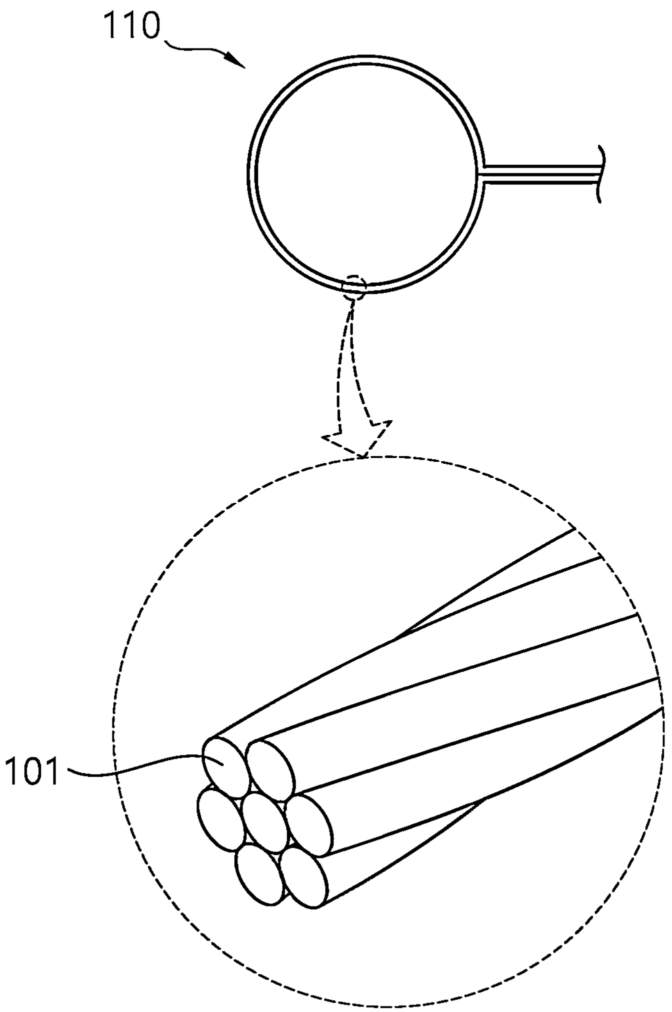

[FIG. 4]
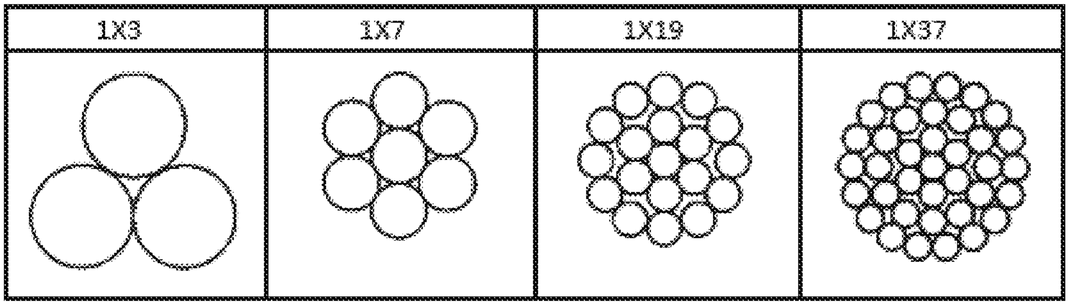

[FIG. 5]
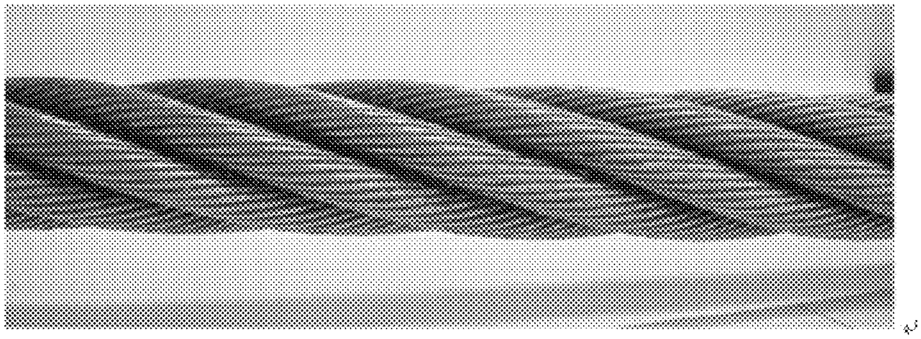
(a)
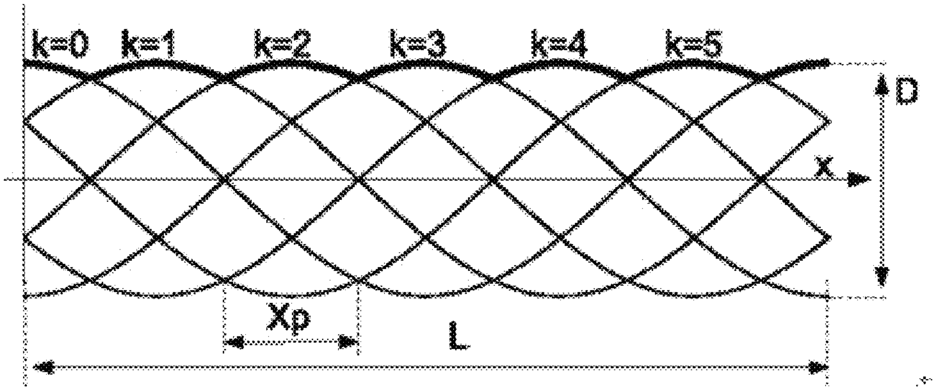
(b)

[FIG. 6]
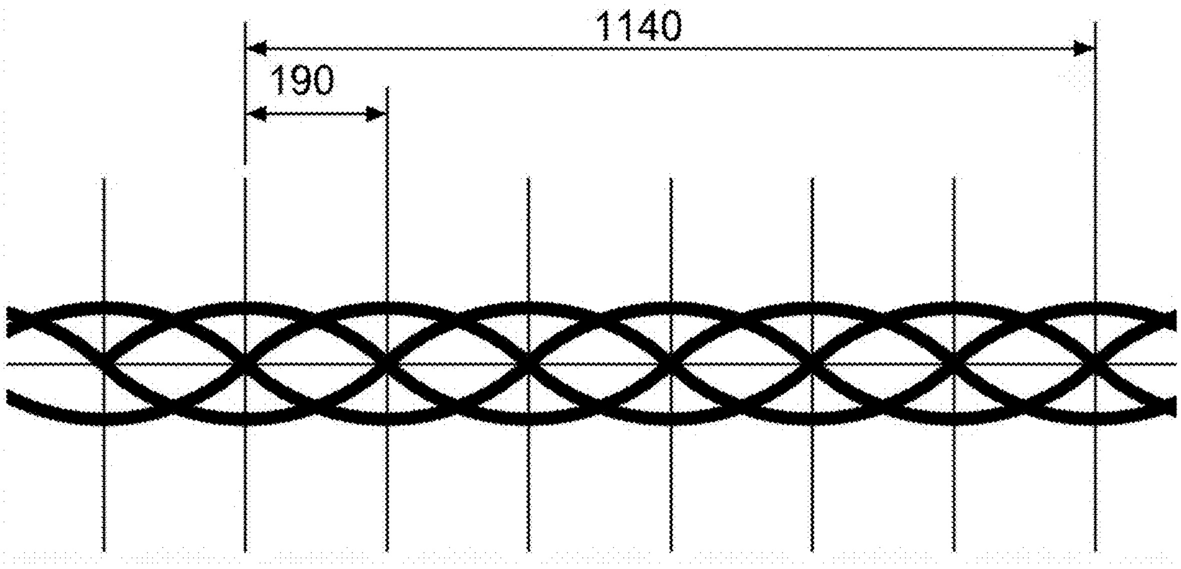

[FIG. 7]
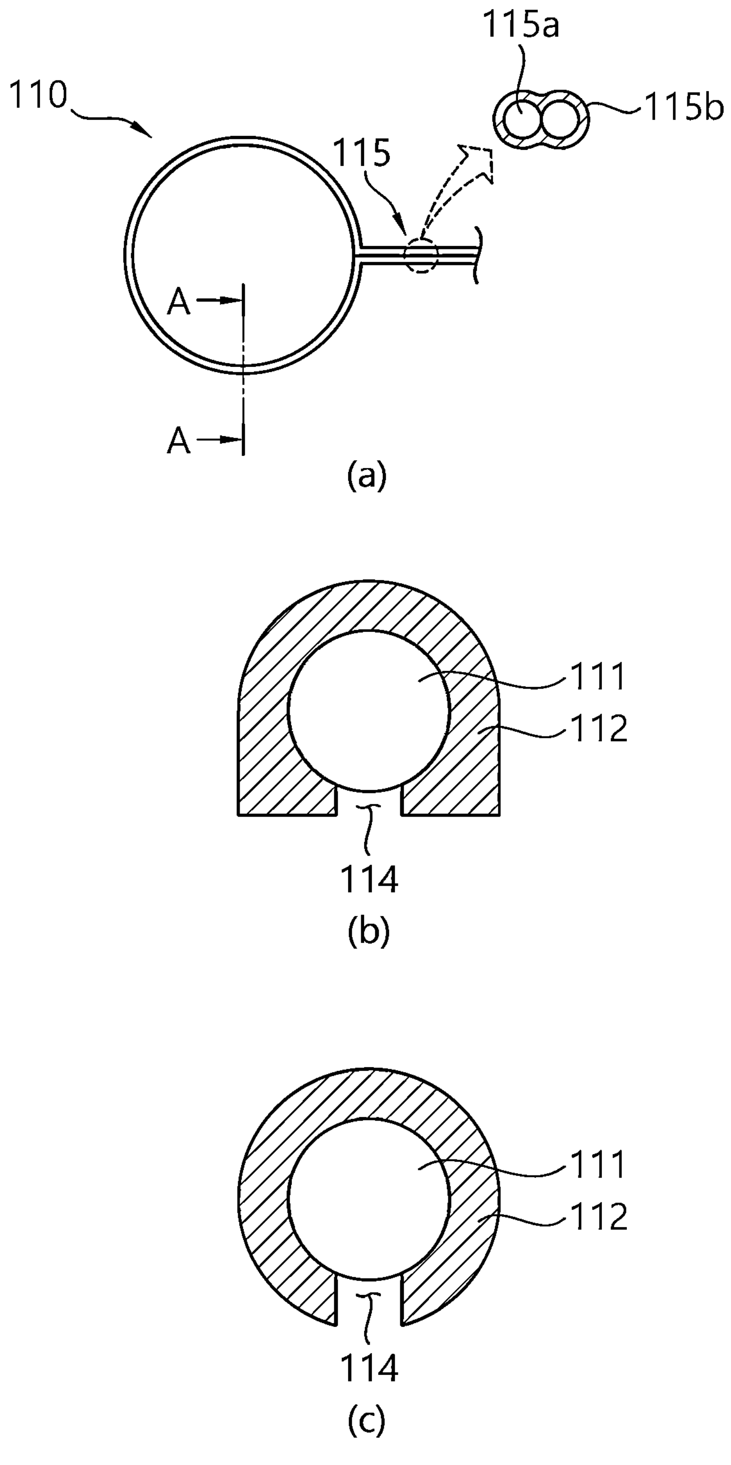

[FIG. 8]
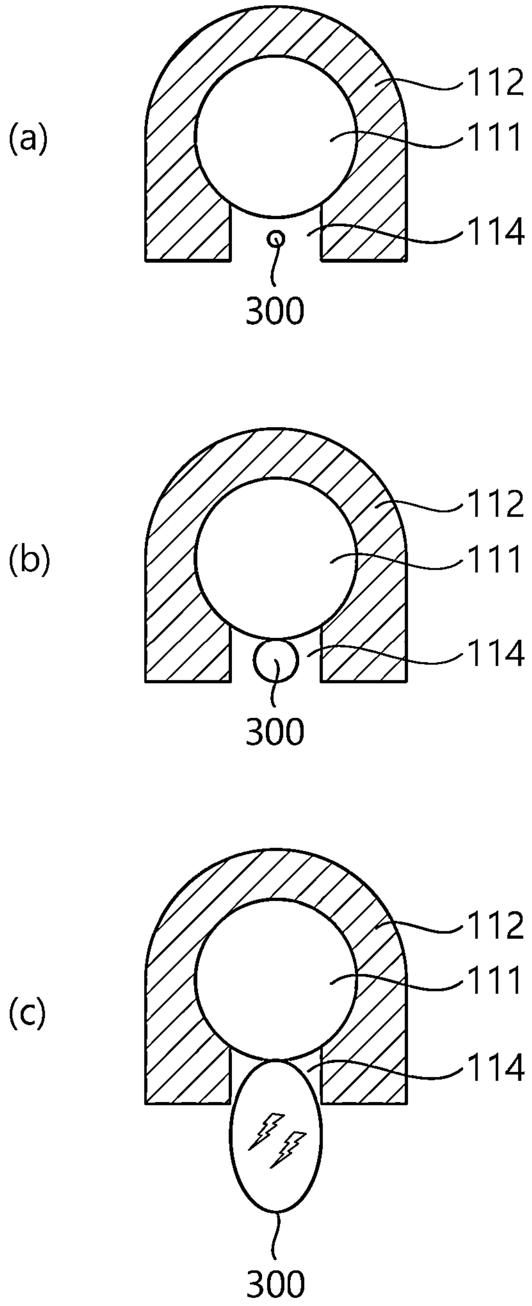

[FIG. 9]
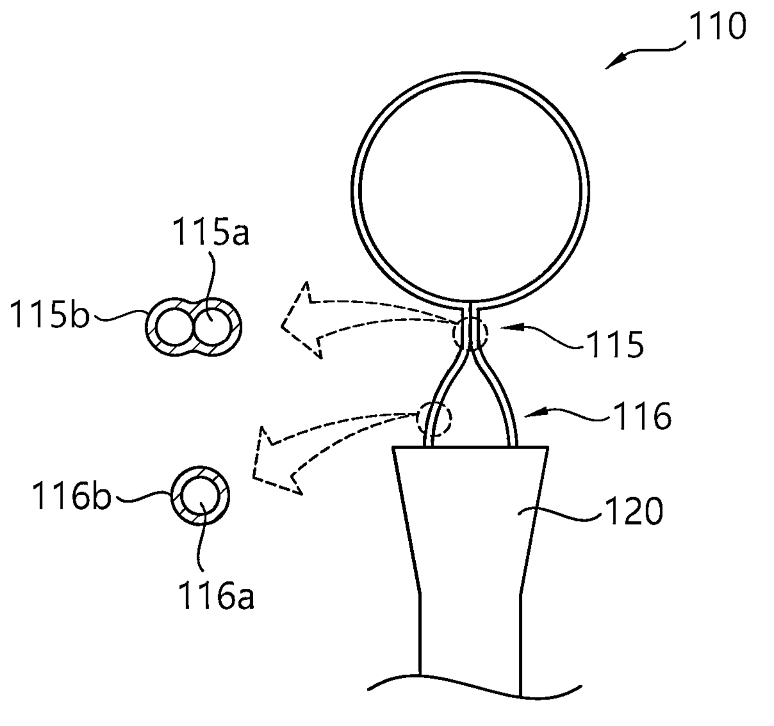

[FIG. 10]
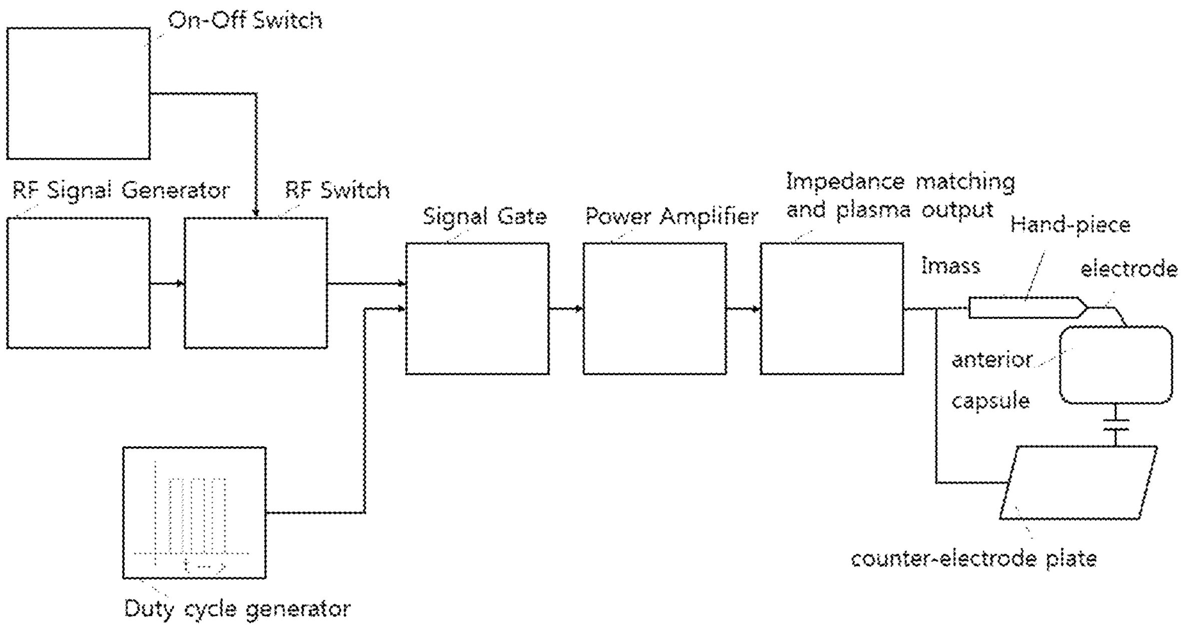

[FIG. 11]
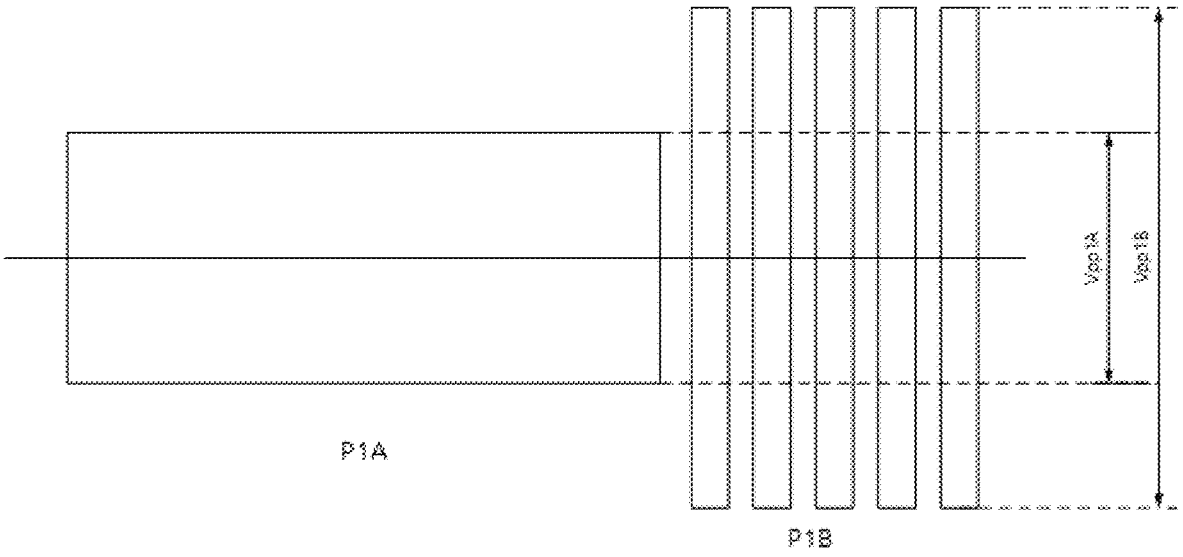

[FIG. 12]
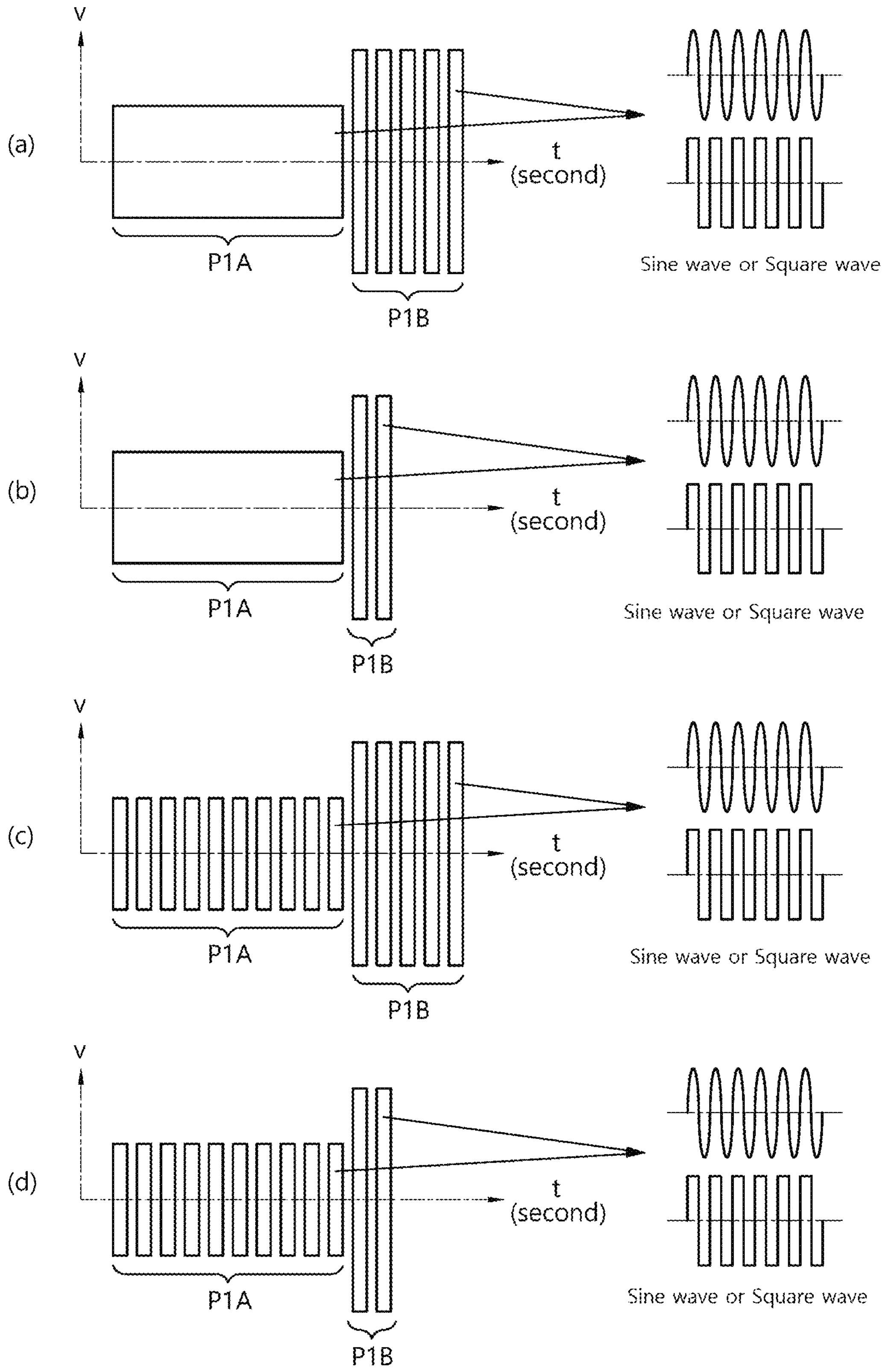

CAPSULORHEXIS APPARATUS, SURGICAL APPARATUS, AND METHOD FOR APPLYING ELECTRIC PULSE TO SURGICAL APPARATUS

CROSS-REFERENCE TO RELATED APPLICATIONS

The present application is the national stage of International Patent Application No. PCT/KR2020/017546 filed on Dec. 3, 2020, which claims priority to and the benefit of Korean Patent Application No. 10-2019-0165068 filed in the Korean Intellectual Property Office on Dec. 11, 2019, the entire contents of which are incorporated herein by reference.

BACKGROUND

1. Field of the Invention

The present disclosure relates to a capsulotomy apparatus, a surgical apparatus, and a method for applying an electric pulse thereto, and more particularly, to a capsulotomy apparatus, a surgical apparatus, and a method for applying an electric pulse thereto for making an incision in tissue using resistive heat or plasma that is caused by electrical energy applied to a cutting electrode.

2. Discussion of Related Art

Making an incision in living tissue using a cutting electrode that receives energy from a power source is a technique that is being successfully employed, e.g., in the field of electrosurgery. Typical electrosurgical devices apply an electrical potential difference or a voltage difference between a cutting electrode and a patient's grounded body (monopolar arrangement) or between a cutting electrode and a return electrode (bipolar arrangement) to deliver electrical energy to tissue.

A cut-off voltage is applied either as a continuous train of high frequency pulses, typically in the radio frequency (RF) range, or as direct current (DC). Depending on the conditions, the application of a voltage to a monopolar electrode or between the cutting electrode and return electrode of a bipolar electrode produces a number of physical phenomena.

Most related art devices use one of these phenomena to perform the cut. For example, U.S. Pat. No. 5,088,997 also teaches the use of a stream of gas for coagulating or cutting biological tissue.

U.S. Pat. No. 6,352,535 discloses a method and device for electro microsurgery that uses high voltage electrical discharges of sub-microsecond duration in a physiological electrolyte environment to produce cavitation bubbles. U.S. Pat. No. 6,364,877 also describes the use of high frequency pulses applied in a continuous manner. U.S. Pat. Nos. 5,697,090 and 5,766,153 suggest a configuration in which a continuous train of high frequency pulses is pulsed at a rate sufficient to cool the electrode.

Most electrosurgical devices described above rely on a gas jet, an arc discharge, or cavitation bubbles to cut, coagulate, or ablate tissue.

However, the electrosurgical methods and devices of the related art documents generally have difficulty in controlling the depth of tissue damage (necrosis) or the direction in the tissue being treated. Such imprecise cutting methods cause tissue necrosis extending up to 1,700 μm into surrounding tissue in some cases.

In particular, in the case of ophthalmic surgery such as cataract surgery, incision control is more important in that the tissue itself is very soft and cavitation bubble production and plasma discharge should not cause damage to be transmitted to the tissue surrounding the incision.

A cataract is a disease in which, due to opacity in the crystalline lens, light is unable to pass through the crystalline lens and thus an object appears blurred. Referring to FIG. 1, an eye (1) consists of a cornea (10), a crystalline lens (20), a crystalline lens capsule (30), an iris (40), a sclera (50), and the like. The cornea (10) is formed to surround the outside of the sclera (50) and is made of a transparent, avascular tissue to refract light, and the crystalline lens (20) is colorless and transparent and serves as a lens of a camera.

According to a widely known method of cataract surgery, an incision is made in the crystalline lens capsule surrounding the crystalline lens to fragment the crystalline lens located therein, and then, simultaneously, the fragmented crystalline lens is suctioned and discharged to the outside and an artificial crystalline lens is inserted to be substituted therefor.

Describing the surgical method with reference to the eye structure illustrated in FIG. 1, an incision with a width of about 2 to 3 mm is made in the cornea (10), an incision tool is inserted through the incision area to make an incision in a front surface of the crystalline lens capsule, that is, the anterior capsule, and the crystalline lens is fragmented using ultrasonic emulsification.

However, since this surgery requires inserting an incision tool into a very narrow area and accurately and neatly making a circular incision of an appropriate size in the anterior capsule while not causing damage to the cornea, iris, and the like that are near the anterior capsule, the level of difficulty of the surgery is very high. Development of various electrosurgical tools is being attempted to address such surgical difficulty, but a structure of an incision electrode that is efficient and capable of making an incision only in a desired area without causing damage to surrounding tissue or an applied voltage suitable for the structure has not been developed.

SUMMARY OF THE INVENTION

The present disclosure is directed to providing a surgical apparatus having a cutting electrode structure for an efficient incision in tissue.

The present disclosure is also directed to providing an electrosurgical apparatus having excellent incision quality due to, while an incision is being made in a tissue, minimizing an influence on a surrounding tissue and concentrating electrical energy only to an area requiring an incision through the form of an incision electrode and/or control of an applied voltage.

The present disclosure is also directed to providing a surgical apparatus having an incision electrode structure that is capable of symmetrically distributing deformation during elastic deformation and making a circular incision without any radial defects in a direction toward a neck part.

A capsulotomy apparatus according to an embodiment of the present disclosure, which is an apparatus inserted into an incision site of the cornea to make an incision in the anterior capsule that surrounds the crystalline lens, includes an electrode part that is formed in the shape of a loop and configured to be inserted into an incision site of the cornea to make a circular incision in the anterior capsule located below the cornea.

The electrode part may be formed by a wire rope made by twisting a plurality of strands, and the wire rope may have pitches at predetermined intervals.

The capsulotomy apparatus may further include a generator electrically connected to the electrode part to apply an electric pulse for capsulotomy. The electric pulse may consist of a first pulse group and a second pulse group, and the first and second pulse groups may each include a plurality of mini-pulses.

A peak voltage of the second pulse group may be 2.5 times to 3 times a peak voltage of the first pulse group.

The wire rope may form the loop-shaped electrode part and a neck part that extends from one area of the electrode part, the neck part may extend as portions of the wire rope at both ends of the electrode part come into contact in a straight form, and an outer surface of the neck part may be coated with an insulating layer.

The neck part formed by one area of the wire rope may have one end connected to the electrode part and the other end branched to form a leg part, and the leg part may be fixed and coupled to a moving member.

The electrode part may include an electrode made of an electrically conductive material and an insulating layer coated on an outer surface of the electrode, and the insulating layer may be formed on upper and side surfaces of the electrode.

The insulating layer on the side surface of the electrode may extend downward so that a bottom surface of the electrode that is not coated may, when applied to face a living tissue, be disposed to be spaced a predetermined distance apart from the tissue.

A surgical apparatus for making an incision in a living tissue according to another aspect of the present disclosure includes a hand piece including a loop-shaped electrode part and a generator configured to transmit electrical energy to the electrode part.

The generator may apply electric-field pulse waveforms made of two consecutive pulse groups to the electrode part.

The two consecutive pulse groups may include a first pulse group and a second pulse group, each pulse group may include mini-pulses, a peak voltage of the first pulse group may be less than a peak voltage of the second pulse group, and a duration of the first pulse group may be longer than a duration of the second pulse group.

The electrode part may be formed in the shape of a loop and may have pitches formed at predetermined intervals along the loop.

The electrode part may include a loop-shaped conductor electrode and an insulating layer coated on the conductor electrode, and the insulating layer may extend by as much as a predetermined length around a non-coated area formed at one side of the conductor electrode.

According to another aspect of the present disclosure, in a surgical apparatus having an electrode part, the electrode part includes an electrode made of an electrically conductive material and an insulating layer coated on an outer surface of the electrode.

The insulating layer may be formed on an entirety of the outer surface of the electrode except for a non-coated area of the electrode, and the insulating layer may extend around the non-coated area of the electrode so that the non-coated area forms a space having an open outer side. More specifically, the insulating layer may extend around the non-coated area of the electrode to form both sidewalls of the non-coated area and form a space having one open surface.

According to another aspect of the present disclosure, a method of applying electrical energy composed of radiofrequency (RF) pulses to a probe electrode of an incision apparatus by using a generator configured to supply electrical energy includes applying a first pulse group and applying a second pulse group.

The total duration of application of the first pulse group and the second pulse group may be in a range of 1 ms to 200 ms, and a duration of the second pulse group may be ¼ to ⅔ of a duration of the first pulse group.

The first pulse group and the second pulse group may each include RF mini-pulses, and a voltage amplitude of the first pulse group may be less than or equal to 60%, or more specifically, in a range of 10% to 60%, of a voltage amplitude of the second pulse group.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 1 is a view schematically illustrating the structure of a human eye (1);

FIG. 2 is a schematic perspective view of a hand piece (100) and a generator (200) configured to supply an electric pulse to the hand piece (100) of a surgical apparatus according to an embodiment of the present disclosure;

FIG. 3 shows a cross-section of a loop-shaped electrode part (110) of the hand piece (100) and an enlarged perspective view of a portion of a side surface of the electrode part (110) of the surgical apparatus according to an embodiment of the present disclosure;

FIG. 4 is a structural diagram illustrating various cross-sections of a wire rope forming the loop-shaped electrode part (110) according to an embodiment of the present disclosure;

FIG. 5 shows a picture and a conceptual diagram for describing a twisting structure of strands constituting the wire rope forming the loop-shaped electrode part (110) according to an embodiment of the present disclosure;

FIG. 6 is a graph showing an incision by the loop-shaped electrode part (110) having pitch spots according to an embodiment of the present disclosure;

FIG. 7 shows a top view and longitudinal cross-sectional views of a structure of a loop-shaped electrode part (110) according to another embodiment of the present disclosure;

FIG. 8 is a view schematically illustrating longitudinal cross-sections of the loop-shaped electrode part (110) and the production and discharge of cavitation bubbles in a biological fluid environment at lower portions of the longitudinal cross-sections according to another embodiment of the present disclosure;

FIG. 9 is a view schematically illustrating a structure of a loop-shaped electrode part (110), a neck part (115), a leg part (116), and a moving member (120) according to still another embodiment of the present disclosure;

FIG. 10 is an electrical block diagram of the entire system including a generator (200), the electrode part (110), a tissue, and a counter-electrode plate according to another embodiment of the present disclosure;

FIG. 11 is a graph showing a first embodiment of pulse waveforms applied to the electrode part (110) by the generator (200) of the present disclosure; and FIG. 12 is a graph showing various pulse waveforms applied to the electrode part (110) by the generator (200) of the present disclosure.

DETAILED DESCRIPTION OF EXEMPLARY EMBODIMENTS

Hereinafter, a surgical apparatus and a method of applying an electric field thereto according to an embodiment of the present disclosure will be described with reference to the accompanying drawings. In this process, thicknesses of lines, sizes of elements, or the like that are illustrated in the drawings may have been exaggerated for clarity and convenience of description. Also, the terms used herein are terms defined in consideration of functions in the present disclosure and may vary according to an intention or practice of a user or an operator. Therefore, the terms should be defined on the basis of the content throughout the specification.

Also, in describing the embodiments of the present disclosure, when detailed description of a known related configuration or function is deemed to hinder the understanding of the embodiments of the present disclosure, the detailed description thereof will be omitted. In addition, although the embodiments of the present disclosure will be described below, the technical idea of the present disclosure is not limited thereto, and the embodiments may be modified and embodied in various other ways by those of ordinary skill in the art.

Throughout the specification, when a certain part is described as being "connected" to another part, this not only includes a case in which the certain part is "directly connected" to the other part but also includes a case in which the certain part is "indirectly connected" to the other part while another element is present therebetween. Throughout the specification, when a certain part is described as "including" a certain element, unless particularly stated otherwise, this indicates that the certain part may further include another element instead of excluding another element. In addition, in describing elements of the embodiments of the present disclosure, terms such as first, second, A, B, (a), and (b) may be used. Such terms are only used to distinguish one element from another element, and the essence, order, sequence, or the like of the corresponding element is not limited by the terms.

Generally, an electrosurgical apparatus includes a hand piece and a generator configured to supply electrical energy to the hand piece.

Since the best mode of the present disclosure is implemented as a capsulotomy apparatus for cataract surgery, hereinafter, a capsulotomy apparatus will be described for convenience of description. However, the description does not limit the surgical apparatus of the present disclosure to the capsulotomy apparatus, and the following configurations may also be applied to other ophthalmic surgical apparatuses or surgical apparatuses for making an incision in human or animal tissue.

Referring to FIG. 2, a capsulotomy apparatus according to an embodiment of the present disclosure includes a hand piece 100 and a generator 200 electrically connected to an electrode part 110 of the hand piece 100 to supply electrical energy, e.g., radiofrequency (RF) pulses, thereto.

The hand piece 100 is an apparatus having a front end inserted into an incision site of a cornea 10 to make an incision in a crystalline lens capsule 30 surrounding a crystalline lens 20. The hand piece 100 may have the shape of a pen as a whole to be easily gripped by a user and to facilitate surgery. The hand piece 100 may include the electrode part 110 having the shape of a loop, a neck part 115 having one end connected to the loop-shaped electrode part 110, a moving member 120 connected to the other end of the neck part 115, a guide portion 130 having a nozzle-type insertion part, a body 140, and a sliding button 150.

According to an embodiment of FIG. 2 of the present disclosure, the electrode part 110 formed in the shape of a closed loop has elasticity and conductivity, and both ends of the loop forming the electrode come into contact with each other at one area of the electrode and extend in a radial direction outward from the electrode to form the neck part 115. Therefore, one end of the neck part 115 is connected to the electrode part 110 having a circular shape, and the other end of the neck part 115 is fixed and coupled to the moving member 120.

The guide portion 130 including a nozzle-type insertion part at a front end is configured so that, while an incision is being made in the crystalline lens capsule, at least a portion of the insertion part at the front end is inserted into the incision site of the cornea. The body 140 is coupled to a rear end of the guide portion 130.

The loop-shaped electrode part 110 is configured to be stored at the rear of the guide portion 130 or in the body 140 and to slide in the body together with the moving member to pass through the insertion part and be unfolded into an anterior chamber of the eye in order to make an incision in the crystalline lens capsule.

The sliding button 150 disposed at one side of the body 140 is configured to be connected to the moving member 120 to slide the moving member 120 and the electrode part 110. For example, the moving member 120 and the electrode part 110 may slide due to manipulation of the sliding button 150 which is able to slide back and forth along a slot formed in the body 140.

In this way, the loop-shaped electrode part 110 may be configured to be inserted into the incision site of the cornea 10 and make a circular incision in the anterior capsule, which is disposed below the cornea 10, using resistive heat or a plasma stream.

When an RF electric field supplied from the generator 200 is applied to the loop-shaped electrode part 110, energy is transmitted to an electrolyte of the crystalline lens capsule 30 that comes into contact with the loop-shaped electrode part 110, and resistive heat and/or plasma is generated. This process causes the tissue of the anterior capsule to be heated or degenerated. By applying electrical energy in a still state in which the electrode is disposed at an appropriate position on the anterior capsule, a circular incision may be made within a short time.

The generator is electrically connected to the moving member 120 which is made of a conductor, and thus high-frequency power is transmitted to the conductive loop-shaped electrode part 110 connected to the moving member.

Meanwhile, the loop-shaped electrode part 110 should be unfolded again and restored to its original circular shape after being deformed due to passing through the guide portion 130 including the nozzle-type insertion part. Thus, the loop-shaped electrode part 110 should have elasticity and a restoration force.

Referring to FIG. 3, the loop-shaped electrode part 110 and the neck part 115 are formed using a wire rope made of a plurality of metal element wires or metal strands twisted together. The wire rope has a structure in which a plurality of strands are twisted together. For example, the wire rope may have a structure in which a plurality of strands are twisted together at an outer side of a rope core disposed at the center.

Referring to FIG. 4, various cross-sections of the wire rope forming the loop-shaped electrode part 110 are shown. From the left side of FIG. 4, a 1×3 structure in which three strands constitute a single wire rope, a 1×7 structure in which seven strands are twisted together to constitute a single wire rope, a 1×19 structure, and a 1×37 structure are sequentially disclosed.

According to an embodiment of the present disclosure, a wire rope having the 1×7 structure forms the loop-shaped electrode, but a wire rope having another structure may also be used. Meanwhile, each strand may have a structure in which element wires of the same diameter or different diameters are twisted in a single layer or multiple layers, but may also be made of a single wire.

The structure of the wire rope made of a plurality of conductive metal strands twisted together has higher elasticity and restoration force as compared to a wire made of a single strand. Thus, the electrode part formed using the wire rope that passes through the nozzle-type insertion part has an excellent restoration force.

FIG. 5A is a picture of an exterior of the wire rope made of a plurality of strands twisted together, and FIG. 5B is a conceptual diagram showing a twisting structure of each strand from a lateral end.

According to an embodiment of the present disclosure, the cutting electrode part 110 has the form of a wire rope electrode having a circular transverse cross-section as a whole. A material of the wire rope electrode may be any suitable conductor such as a metal or an alloy made of stainless steel, tungsten, titanium, and molybdenum. The wire rope has the 1×7 structure and a lay pitch of 1.14 mm.

When the electrode part 110 made of the wire rope is unfolded into the anterior chamber of the eye and disposed at an upper portion of the anterior capsule, a lower portion of the wire rope is partially dipped in a biological electrolytic solution. Here, the wire rope electrode having pitches at predetermined intervals due to the strands being twisted together is placed close to the tissue, and then the generator is operated to apply an electric field thereto.

Describing the structure of the strands and the wire rope in detail with reference to FIG. 5B, a k=0 strand recovers its original phase while moving a distance of a lay pitch L. That is, the k=0 strand rotates 360° while moving the distance L horizontally. The same applies for other strands k=1, k=2, k=3, k=4, and k=5.

According to an embodiment of the present disclosure illustrated in FIG. 5, since the lay pitch L of the wire rope is 1.14 mm and a total of six strands except for a core strand are twisted together, a spot interval Xp is 0.19 mm (=1.14/6). Due to the twisting of the strands forming the wire rope electrode, a tissue adjacent to the loop-shaped electrode part 110, specifically, a relative distance between an area of a tissue and an area of the electrode that faces the area of the tissue, regularly changes. That is, the circular electrode is configured to have regular pitches like valleys and ridges.

Here, a pitch spot is an area of the electrode part where a distance to the facing area of the tissue is the shortest. A plurality of pitch spots are disposed at predetermined intervals due to regular twisting of the strands, and an interval between the spots is the pitch spot interval Xp.

In the capsulotomy apparatus, when the wire rope electrode is disposed at an upper portion of the anterior capsule, pitch spots are arranged at predetermined intervals on a bottom surface of the circular electrode, and a distance from the anterior capsule therebelow also regularly changes accordingly.

When an appropriate electric field (which will be described below) is applied, incision bubbles are formed around the pitch spots, which are formed due to twisting of the strands, and an incision is performed at predetermined spot intervals.

For example, when the circular electrode has a diameter of 5 mm, the overall length (circumference) of the circular electrode is 15.7 mm (5 mm×3.14), and the total number of spots is 82.6 ((15.7/1.14)×6=13.77×6).

FIG. 6 is a graph showing an incision form produced due to the loop-shaped electrode part having a spot pitch of 0.19 mm. The horizontal axis indicates a distance along the circumference of the circular electrode, and the vertical axis indicates a vertical height of the tissue. Here, an incision bubble area formed around the pitch spot of 0.19 mm is shown with bold lines. A vertical amplitude of the incision bubble area is 100 μm, which can be seen as an incision diameter. Here, when incision bubbles produced downward are produced to have a size of about 100 μm, an entire incision surface is formed.

In this way, by applying electric pulses to the loop-shaped electrode part, in which pitch spots are formed at predetermined intervals, and forming incision bubbles around the spots of the electrode, it is possible to improve energy efficiency and make a completely circular incision in the anterior capsule within a short time while minimizing damage.

Meanwhile, a pitch multiple is defined as (lay pitch of wire rope)/(diameter of wire rope), and a typical wire rope has a pitch multiple in a range of 5 to 8. For elastic restoration of the wire rope passing through the insertion part, the larger the pitch multiple of the wire rope, the better. However, when the pitch multiple is large, the above-described pitches may be eliminated, and an incision may not be made efficiently. The inventors of the present disclosure have found out that setting the pitch multiple of the wire rope to be in a range of 8 to 12 is desirable for securing elasticity and restorability while allowing an efficient incision in tissue.

In this way, the circular cutting electrode of the present disclosure has regular pitch spots and thus is able to make an incision in a tissue efficiently and safely through forming cavitation bubbles around the spots. According to the embodiment of the present disclosure, the pitches of the circular cutting electrode are due to the wire rope structure made of a plurality of strands being twisted together, but the present disclosure is not limited thereto, and even when the electrode is made of a single-strand wire, a method such as coating may allow the electrode to have a pitch structure.

Hereinafter, still another embodiment of the present disclosure will be described with reference to FIG. 7. The configuration of this embodiment of the present disclosure may be applied to the electrode part 110 formed using the wire rope made of the plurality of strands of FIGS. 3 to 5, but the present disclosure is not limited thereto, and the configuration of this embodiment may also be applied to any other form of cutting electrode part 110.

According to FIG. 7, a loop-shaped electrode part 110 is made of a stainless steel wire rope. The cutting electrode part 110 includes an electrode 111 made of an electrically conductive material and an insulating layer 112 coated on the electrode. The electrode 111 may be a wire rope made of a plurality of strands twisted together but is not limited thereto and may also be a single-strand wire.

Here, the electrode 111 forming the loop-shaped electrode part is coated with the insulating layer 112 made of an electrically insulating material. The insulating layer may be made of any material providing electrical insulation, such as Teflon and polyamide, or a combination thereof.

When the electrode part is applied to a living tissue in which an incision is to be made, that is, applied on the anterior capsule, a bottom surface of the insulating layer may come into contact with the anterior capsule, and a bottom surface of the electrode, which is a non-coated area, may be spaced a predetermined distance apart from an upper surface of the anterior capsule. Various embodiments therefor are disclosed in FIGS. 7 and 8.

FIG. 7A is a top view of the loop-shaped electrode part 110, and FIGS. 7B and 7C are two embodiments of a cross-sectional view taken along line A-A of FIG. 7A. As in the case of FIG. 3, the electrode part 110 and the neck part 115 are made of a single wire rope in which both ends of the electrode part 110 extend from one area of the wire rope toward the outside of the circular loop and come into contact with each other to form the neck part, and an area between both ends of the electrode part 110 forms a circular loop.

The electrode part 110 includes the conductive electrode 111 and the insulating layer 112 coated on the circumference of the electrode, wherein the insulating layer 112 is coated on the electrode 111 except for one area (bottom surface) of the electrode 111.

As illustrated in FIG. 7, the insulating layer 112 extends a predetermined length around a non-coated area of the electrode 111 or is coated with a predetermined thickness on both sides of the non-coated area to prevent direct contact between the bottom portion, which is the non-coated area, of the electrode 111 and the living tissue.

The insulating layer 112 formed on an outer surface of the cutting electrode 111 to which an electric pulse is applied extends from both sides of the non-coated area so that the non-coated area is spaced apart from the living tissue, in which an incision is to be made, when facing the living tissue.

Therefore, when the electrode part 110 of the capsulotomy apparatus is disposed on the anterior capsule, the non-coated area at the lower portion that is formed in a circular shape along the bottom surface of the loop is disposed to face the anterior capsule, and due to the insulating layer 112, the non-coated area is spaced apart from the tissue of the anterior capsule, and a space 114 is formed therebetween.

When the electrode part 110 having the structure illustrated in FIG. 7 is disposed at the anterior capsule, the space 114 at the lower portion is filled with a biological electrolyte, but the tissue of the anterior capsule does not come in direct contact with the electrode 111.

FIG. 8 schematically illustrates plasma development due to production and discharge of cavitation bubbles. Referring to FIG. 8, when RF pulses or other electric fields are applied to the electrode 111, the space facilitates plasma development due to production and discharge of cavitation bubbles. Simultaneously, resistive heat and/or plasma production and an ion movement direction are concentrated downward, that is, in a direction in which the insulating layer disposed at both sides of the non-coated area extends.

As a comparative example, when only the upper surface and both side surfaces are coated but the insulating layer does not extend while a non-coated area partially remains at the lower portion, the coating layer does not cause a separation space to be formed between the non-coated area and the tissue. Thus, the production and discharge of cavitation bubbles is not effective, and further, since electrical energy spreads in a radial direction from an area of the electrode that comes into contact with the tissue, energy for effective incision is not able to be concentrated to a desired area.

On the other hand, the electrode 111 of the present disclosure may be any electrode having a narrow exposed area. Thus, vaporization and ionization may efficiently occur around an exposed surface at the lower portion of the electrode.

This causes current to flow in surrounding tissue, and thus it is possible to prevent unnecessary tissue damage and degradation of incision quality that may occur due to the spread of resistive heat or plasma. Further, it is possible to obtain excellent incision quality by applying only an optimal amount of electrical energy to produce plasma and concentrate a stream in a desired direction.

In FIG. 7, the neck part 115 is for mechanical and electrical connection between the moving member 120 and the electrode part. The wire ropes extending from both ends of the loop come into contact with each other at the electrode part and extend outward in a straight line. Here, the circular electrode part 110, the neck part 115, and the moving member may be disposed to be coplanar.

The neck part 115 is configured so that both end portions 115*a* of the wire rope that form the loop-shaped electrode 111 are adhered to each other or come into contact with each other, and an insulating layer 115*b* completely surrounds the outer circumference of the neck part 115. In particular, a portion of the neck part 115 that is connected to the electrode part may be fully coated. This is to prevent an electric field from being applied to an undesired tissue while electrical energy is being supplied to the electrode part.

Meanwhile, according to yet another embodiment of the present disclosure illustrated in FIG. 9, a hand piece includes a loop-shaped electrode part 110, a neck part 115 which extends from the electrode part to support the electrode part, and a leg part 116.

The electrode part 110, the neck part 115, and the leg part 116 are integrally formed by a single wire rope. That is, the wire rope forms the electrode part 110 having the shape of a closed loop, both side areas of the wire rope that extend from one end of the electrode part toward the outside of the electrode part 110 come into contact with each other and extend in a straight line to form the neck part 115, and two leg parts 116 are formed by branching from the neck part 115. One side of the leg part 116 is connected to the neck part 115, and the other side of the leg part 116 is fixed and coupled to the moving member 120.

The neck part serves as a rod that unfolds the loop-shaped electrode part once the electrode part passes through the nozzle-type insertion part, and the leg part has an arch structure, in which a portion connected to the neck part is the peak of the arch, to prevent bending of the neck part. A pointed arch, a lancet arch, an ogee arch, or the like may be applied as the arch structure. Due to the arch structure, a deformation force on the neck part and the loop-shaped electrode part when the electrode part passes through the narrow insertion part is symmetrically distributed, thus facilitating restoration to the original circular shape.

Hereinafter, an electric pulse applied by the generator of the present disclosure will be described with reference to FIGS. 10 and 11. FIG. 10 is a block diagram illustrating an electrical system including elements of the generator, the electrode disposed at the anterior capsule through the hand piece, and a counter-electrode plate that comes into contact with another part of the body. The generator 200 is connected to the electrode part 110 and the counter-electrode plate (return electrode).

The generator has an RF signal generator for generating a voltage to be applied between the electrode part and the counter-electrode plate (return electrode). As will be described below, the generator has a pulse controller for controlling a electric pulse according to a predefined modulation format (pulse system or pulse waveform).

Pulse control includes duration control for adjusting pulse power, a pulse duration, and a pulse interval. When a pulse waveform is applied to the electrode part, a thin layer of plasma may be formed around the circular cutting part. Using power, a voltage is applied to the electrode disposed in the electrolytic solution to form plasma bubbles in a circumferential direction of the electrode, and the bubbles come into contact with the tissue of the anterior tissue to cause discharge toward the inside of the bubbles so that the tissue of the anterior capsule is cut in the circumferential direction of the loop-shaped electrode part.

FIG. 11 illustrates a first embodiment of electric-field waveforms generated by the generator. The graph shown in FIG. 11 has been rotated 90°. The horizontal axis indicates the strength of the electric field while the vertical axis indicates time.

Electric-field waveforms according to an embodiment of the present disclosure may consist of two consecutive pulse groups and, to make an incision in the anterior capsule, may be applied to the electrode part of the hand piece that has any one of the structures illustrated in FIGS. 2 to 9 or a combined structure thereof to make an incision in the anterior capsule within a short time. An incision is made in the anterior capsule by only using two continuous square pulses without requiring additional pulse waveforms for making an incision in the anterior capsule.

Referring to FIG. 11, the first embodiment of the pulse waveforms of the present disclosure consists of a first pulse group and a second pulse group. A first pulse group P1A lasts for a first time, and a second pulse group P1B lasts for a second time. The first time is longer than the second time, and in an embodiment, the first time and the second time have a ratio of 7:3. In another embodiment, the ratio may be 2:1, 3:1, 3:2, 4:3, 5:2, 5:3, 5:4, 7:2, and 7:4. Preferably, the first time/second time may be in a range of 1.2 to 3.5.

The first pulse group HA and the second pulse group P1B both have continuous mini-pulses therein, and the mini-pulses may be sine waves or square waves having a frequency in a range of 10 MHz to 400 MHz. The mini-pulses have a frequency of, for example, 2 MHz or 5 MHz. Also, the first pulse group P1A has a higher peak voltage than the second pulse group P1B. In the embodiment of FIG. 11, the second pulse group P1B has a voltage that is about 2.8 times higher than the first pulse group P1A.

A primary voltage value Vpp1A of the first pulse group and a secondary voltage value Vpp1B of the second pulse group P1B are adjusted by the RF signal generator and a power amplifier.

As an example of the present embodiment, the primary voltage value Vpp1A may be 300 V, and the secondary voltage value Vpp1B may be 850 V. However, the secondary voltage value Vpp1B may be 1 kV or higher while the primary voltage value Vpp1A is 300 V.

Here, the pulses of the first pulse group P1A are pulses for supplying sufficient power until water molecules evaporate after being rapidly heated, and the pulses of the second pulse group P1B are pulses for suppressing Joule heat when an incision occurs due to vaporization and plasma discharge so that a temperature increase of tissue of the patient's eye is suppressed.

The first pulse group P1A may have continuous pulses or a plurality of waveforms formed into pulses, and the second pulse group P1B is a plurality of waveforms formed into pulses.

With regards to pulse waveforms illustrated in FIG. 12, as described above, the time during which a voltage (y-axis) is applied to the incision electrode part is in a range of 1 ms to 200 ms (x-axis). For example, the time may be 50 ms, 60 ms, 70 ms, 80 ms, 90 ms, and 100 ms. In this way, by applying voltages having the illustrated pulse waveforms, Joule heat occurs at the incision electrode, and water molecules present in the vicinity of the incision electrode are rapidly heated and then evaporated. In an aqueous humor, evaporation bubbles are formed around the incision electrode. By this, circular evaporation bubbles are formed in the circumferential direction of the incision electrode.

When the evaporation bubbles formed as above come into contact with the incision electrode, high voltage is also applied to the inside of the evaporation bubbles, and plasma is formed. In this way, the evaporation bubbles that contain plasma are formed in the circumferential direction of the circular cutting electrode.

Also, the evaporation bubbles come into contact with the anterior capsule. Also, through a plasma layer inside the evaporation bubbles, current flows from the cutting electrode to the return electrode, and discharge (hereinafter referred to as "plasma discharge") occurs inside the evaporation bubbles.

In this way, since the evaporation bubbles are brought into contact with the anterior capsule and plasma discharge occurs inside the evaporation bubbles, a large amount of current instantaneously flows locally in the evaporation bubbles. As a result, a portion of the anterior capsule, which comes into contact with the circular evaporation bubbles in which plasma discharge occurs, evaporates and thus a circular incision is made in the anterior capsule. In this way, in the present embodiment, a circular incision is made in the anterior capsule in the circumferential direction of the incision electrode. In this process, the pulses of the first pulse group HA are pulses for supplying sufficient power until water molecules evaporate after being rapidly heated, and the pulses of the second pulse group P1B are pulses for suppressing Joule heat when an incision occurs due to vaporization and plasma discharge so that a temperature increase of the patient's eye is suppressed.

FIG. 12 illustrates various modified examples of applied pulses. The first pulse group may include a plurality of sub-pulse groups or may be a single pulse group. The second pulse group includes a plurality of sub-pulse groups. In this case, each sub-pulse group includes RF mini-pulses. Meanwhile, as illustrated in FIG. 12, the plurality of sub-pulse groups may be square waves to which a voltage is not applied after being applied for a predetermined amount of time.

A surgical apparatus according to one aspect of the present disclosure has high efficiency and concentrates energy only to a desired area and only in a desired direction, thus having excellent tissue incision quality and facilitating control.

According to another aspect of the present disclosure, by distributing a deformation force, it is possible to make a completely circular incision while securing an excellent restoration force.

According to still another aspect of the present disclosure, it is possible to make an incision while minimizing damage to surrounding tissue.

INDUSTRIAL APPLICABILITY

The apparatus of the present disclosure is a surgical apparatus for cataract surgery and can be widely used in the field of medical equipment.

What is claimed is:

1. A capsulotomy apparatus for incising an anterior capsule covering a crystalline lens, the capsulotomy apparatus comprising:
   - an electrode part of a circular loop shape configured to be inserted into the incision site of the cornea to make a circular incision in the anterior capsule located below the cornea,
   - wherein the electrode part is formed of a wire rope and has a plurality of pitch spots arranged at regular intervals on a bottom surface of the electrode part, and
   - wherein each of a plurality of pitch spots is an area of the electrode part where a distance to a living tissue of the anterior capsule is shortest when the electrode part is inserted through the incision site of the cornea and positioned above the anterior capsule,
   - wherein:
   - the wire rope comprises a plurality of twisted strands,
   - the plurality of pitch spots are formed due to regular twisting of the strands to form incision bubbles around each of the plurality of pitch spots by applying electric field to the electrode part and to perform incision at regular spot intervals,
   - the plurality of twisted strands of the wire rope recover original phase while moving a distance of a lay pitch,
   - a pitch multiple is defined by dividing a lay pitch of the wire rope by a diameter of the wire rope,
   - the wire rope has a pitch multiple in a range of 8 to 12,
   - the electrode part includes an electrode made of an electrically conductive material and an insulating layer coated on an outer surface of the electrode, and
   - the insulating layer surrounds upper and side surfaces of the electrode, and opposite ends of the insulating layer are positioned lower than a bottom surface of the electrode such that an empty concave groove is formed by the opposite ends of the insulating layer and the bottom surface of the electrode.

2. The capsulotomy apparatus of claim 1, further comprising a generator electrically connected to the electrode part to apply an electric pulse for capsulotomy,
   - wherein the electric pulse consists of a first pulse group and a second pulse group, the second pulse group is applied subsequently after application of the first pulse group, and the first and second pulse groups include respectively a plurality of mini-pulses, and
   - a peak voltage of the plurality of mini-pulses of the second pulse group is 2.5 times to 3 times a peak voltage of the plurality of mini-pulses of the first pulse group.

3. The capsulotomy apparatus of claim 2,
   - wherein the total duration of application of the first pulse group and the second pulse group is in a range of 1 ms to 200 ms,
   - a duration of the second pulse group is ¼ to ⅔ of a duration of the first pulse group,
   - the first pulse group and the second pulse group each include RF mini-pulses, and
   - a voltage amplitude of the first pulse group is less than or equal to 60% of a voltage amplitude of the second pulse group.

4. The capsulotomy apparatus of claim 1, wherein:
   - the wire rope forms the electrode part of a circular loop shape and a neck part that extends from one area of the electrode part; and
   - the neck part extends as portions of the wire rope at both ends of the electrode part come into contact in a straight form, and the insulating layer is formed on an outer surface of the neck part.

5. The capsulotomy apparatus of claim 4, wherein the neck part formed by one area of the wire rope has one end connected to the electrode part and the other end branched to form a leg part, and the leg part is fixed and coupled to a moving member.

6. The capsulotomy apparatus of claim 1, wherein:
   - the insulating layer is formed on the upper and side surfaces of the electrode so that, when the electrode part is applied to face the living tissue in which an incision is to be made, a bottom surface of the insulating layer comes into contact with the living tissue while the bottom surface of the electrode that is not coated is spaced a predetermined distance apart from the tissues.

7. The capsulotomy apparatus of claim 1, wherein:
   - the incision bubbles are formed around the plurality of pitch spots by applying radiofrequency (RF) pulses to the electrode part.

8. The capsulotomy apparatus of claim 1, wherein the regular intervals at which the plurality of pitch spots arranged are identical to each other.

9. A surgical apparatus for making an incision in a living tissue, the surgical apparatus comprising:
   - a hand piece including an electrode part of circular loop-shape; and
   - a generator configured to transmit electrical energy to the electrode part,
   - wherein the electrode part is formed of a wire rope and has a plurality of pitch spots arranged at regular intervals on a bottom surface of the electrode part,
   - wherein each of a plurality of pitch spots is an area of the electrode part where a distance facing living tissues is shortest when the electrode part is positioned above the living tissues,
   - wherein the generator applies electric pulse wave made of two consecutive pulse groups to the electrode part, and
   - the two consecutive pulse groups include a first pulse group and a second pulse group, each pulse group includes mini-pulses, a peak voltage of the first pulse group is less than a peak voltage of the second pulse group, and a duration of the first pulse group is longer than a duration of the second pulse group,
   - wherein:
   - the wire rope comprises a plurality of twisted strands,
   - the plurality of pitch spots are formed due to regular twisting of the strands,
   - the plurality of twisted strands of the wire rope recover original phase while moving a distance of a lay pitch,
   - a pitch multiple is defined by dividing a lay pitch of the wire rope by a diameter of the wire rope,
   - the wire rope has a pitch multiple in a range of 8 to 12,
   - the electrode part includes an electrode made of an electrically conductive material and an insulating layer coated on an outer surface of the electrode, and
   - the insulating layer surrounds upper and side surfaces of the electrode, and opposite ends of the insulating layer are positioned lower than a bottom surface of the electrode such that an empty concave groove is formed by the opposite ends of the insulating layer and the bottom surface of the electrode.

10. The surgical apparatus of claim 9, wherein incision bubbles are formed around each of a plurality of pitch spots by applying an electric pulse to the electrode part.

11. The surgical apparatus of claim 9, wherein:

the insulating layer extends by as much as a predetermined length around a non-coated area formed at one side of the conductor electrode.

12. The surgical apparatus of claim 9, wherein:

the insulating layer is formed on an entirety of the outer surface of the electrode except for a non-coated area of the electrode; and the insulating layer extends around the non-coated area of the electrode to form both sidewalls of the non-coated area and form the empty concave groove having one open surface.

13. The surgical apparatus of claim 9, wherein the regular intervals at which the plurality of pitch spots arranged are identical to each other.

* * * * *